US012171797B2

(12) United States Patent
Jeong et al.

(10) Patent No.: US 12,171,797 B2
(45) Date of Patent: Dec. 24, 2024

(54) COMPOSITION FOR AMELIORATING PREMENSTRUAL SYNDROME SYMPTOMS, INCLUDING CHRYSANTHEMUM ZAWADSKII EXTRACT

(71) Applicant: GENENCELL INC., Gyeonggi-do (KR)

(72) Inventors: Yong Joon Jeong, Gyeonggi-do (KR); Se Chan Kang, Gyeonggi-do (KR); Jeong Eun Kwon, Gyeonggi-do (KR); Da Eun Lee, Incheon (KR)

(73) Assignee: GENENCELL INC., Gyeonggi-do (KR)

( * ) Notice: Subject to any disclaimer, the term of this patent is extended or adjusted under 35 U.S.C. 154(b) by 57 days.

(21) Appl. No.: 17/637,915

(22) PCT Filed: Sep. 3, 2019

(86) PCT No.: PCT/KR2019/011306
§ 371 (c)(1),
(2) Date: Feb. 24, 2022

(87) PCT Pub. No.: WO2021/045242
PCT Pub. Date: Mar. 11, 2021

(65) Prior Publication Data
US 2022/0280583 A1   Sep. 8, 2022

(51) Int. Cl.
*A61K 36/287*   (2006.01)

(52) U.S. Cl.
CPC .................................. *A61K 36/287* (2013.01)

(58) Field of Classification Search
None
See application file for complete search history.

(56) References Cited

FOREIGN PATENT DOCUMENTS

| CN | 101919979 A | | 12/2010 | |
|---|---|---|---|---|
| JP | 2008019181 A | * | 1/2008 | |
| KR | 960003883 B1 | * | 3/1996 | |
| KR | 20020009340 A | | 2/2002 | |
| KR | 20050058561 A | | 6/2005 | |
| KR | 10-2009-0081860 A | | 7/2009 | |
| KR | 10-2010-0044433 A | | 4/2010 | |
| KR | 20100044433 A | * | 4/2010 | |
| KR | 20110049436 A | | 5/2011 | |
| KR | 101340040 B1 | * | 5/2013 | |
| KR | 10-2013-0076114 A | | 7/2013 | |
| KR | 10-2013-0092256 A | | 8/2013 | |
| KR | 20130086682 A | | 8/2013 | |
| KR | 10-2016-0069208 A | | 6/2016 | |
| KR | 20170134237 A | | 12/2017 | |
| KR | 101841137 B1 | | 3/2018 | |
| KR | 20190038011 A | | 4/2019 | |
| KR | 20190105971 A | | 9/2019 | |
| KR | 10-2045903 B1 | | 11/2019 | |
| KR | 102331317 B1 | | 11/2021 | |
| WO | WO-2018030650 A1 | * | 2/2018 | ........... A23L 33/105 |

OTHER PUBLICATIONS

MediColumn (http://www.medicolumn.com/news/articleView.html?idxno=886) 2015 (Year: 2015).*
Yonhap News Agency (https://en.yna.co.kr/view/AEN20181024007800315) Oct. 24, 2018 (Year: 2018).*
The Health Site (https://www.thehealthsite.com/news/premenstrual-syndrome-premenstrual-dysphoric-disorder-natural-remedies-you-must-try-x0918-607287/) Sep. 25, 2018 (Year: 2018).*
KR20100044433A translated doc (Year: 2010).*
KR101340040B1 translated doc (Year: 2013).*
KR960003883B1 translated doc (Year: 1996).*
Medi Column (Jan. 15, 2015).
NewsWire (May 22, 2008).
Schmidt, P. J., Martinez, P. E., Nieman, L. K., Koziol, D. E., Thompson, K. D., Schenkel, L., . . . Rubinow, D. R. (2017). Premenstrual Dysphoric Disorder Symptoms Following Ovarian Suppression: Triggered by Change in Ovarian Steroid Levels but Not Continuous Stable Levels. American Journal of Psychiatry, 174(10), 980-989. doi:10.1176/appi.ajp.2017.16101113.
J. Halbreich et al. Serum-Prolactin in Women Witi Premenstrual Syndrome, 1976.
Wendy S Biggs , Robin H Demuth, Premenstrual syndrome and premenstrual dysphoric disorder, m Fam Physician. Oct. 15, 2011;84(8):918-924.
A. Imai, S. Ichigo, K. Matsunami, H. Takagi, Premenstrual syndrome: management and pathophysiology, 2015.
An ancient healing system's gifts to the Modern Woman. California College of Ayurveda. (Mar. 2010).
Ramaswamy, S. Ayurveda—An ancient healing system's gifts to the Modern Woman. Research paper, California College of Ayurveda. Mar. 2010, pp. 1-43. See p. 10.
International Search Report issued in PCT/KR2019/011306, dated Mar. 3, 2021.
Austrailian Examination Report dated Jun. 6, 2023, issued during the prosecution of Australian Patent Application No. AU 2019464462.
Lee et al., "Lomens-PO (mixed extracts of Hordeum vulgare and Chrysanthemum Hawadskii) regulate the expression of factors affecting premenstrual syndrome symptoms," Nutrition Research and Pract. 15(6):715-731 (Dec. 2021); https://doi.org/10.4162/nrp.2021.15.6.715; pISSN 1976-1457.eISSN 2005-6163; Korea.

(Continued)

*Primary Examiner* — Aaron J Kosar
*Assistant Examiner* — Jacob A Boeckelman
(74) *Attorney, Agent, or Firm* — Locke Lord LLP; Scott D. Wofsy; Gabrielle L. Gelozin

(57) ABSTRACT

The present invention relates to a composition which is for preventing and ameliorating or treating premenstrual syndrome symptoms, and includes: (a) a *Chrysanthemum zawadskii* extract; (b) a mixture of the *Chrysanthemum zawadskii* extract and a malt extract; or (c) a mixture of the *Chrysanthemum zawadskii* extract, the malt extract, and an aloe extract. Specifically, the present compositions effectively inhibit the secretion of prolactin from pituitary cells, which is a phenomenon that appears during premenstrual syndrome, thereby increasing the secretion of progesterone, which is reduced during the luteal phase of women, and can thus be advantageously used as a composition for preventing and ameliorating or treating women's premenstrual syndrome.

11 Claims, 2 Drawing Sheets

(56) References Cited

OTHER PUBLICATIONS

Kang et al., "*Chrysanthemum zawadskii* var. *latilobum* Extract Inhibits the Production of Nitric Oxide and PGE2 through Inducible Nitric Oxide Synthase (iNOS) and Cyclooxygenase-2(COX-2) in RAW 264. 7 Cells," Biotechnology and Bioprocess Engineering 18: 501-506 (2013); DOI 10.1007/s12257-012-0691-0; Korea.

Kim et al., "The effects of Chrysanthemum zawadskii Herbs," The Korea Journal of Herbology, vol. 4 No. 1, 15-21 (1989); ISSN 1229-1765; Korea.

Yanagi PMS (Premenstrual Syndorome) Premenstrual Syndrome「, 」(Oct. 12, 2016); Japan; retrieved from Dojindo, Kampo Bible for Women, http://www.kanpo-dojindo.co.jp/women/w-vol06「.

* cited by examiner

COMPOSITION FOR AMELIORATING PREMENSTRUAL SYNDROME SYMPTOMS, INCLUDING CHRYSANTHEMUM ZAWADSKII EXTRACT

CROSS-REFERENCE TO RELATED APPLICATIONS

This application is a U.S. National Phase Application filed under 35 U.S.C. § 371, based on International PCT Patent Application No. PCT/KR2019/011306, filed Sep. 3, 2019. The entire contents of this application is incorporated herein by reference.

TECHNICAL FIELD

The present disclosure relates to a composition for ameliorating, preventing, or treating premenstrual syndrome containing a *Chrysanthemum zawadskii* extract as an active ingredient.

BACKGROUND ART

As defined by the International Classification of Disease ([ICD]-10), premenstrual syndrome is diagnosed when at least one of seven symptoms including minor psychological distress, bloating, weight gain, breast tenderness, muscular tension or aches, poor concentration, and changes in appetite occurs only in the luteal phase of the menstrual cycle. Premenstrual syndrome usually occurs within 4-7 days before menstruation, and the symptoms thereof completely disappear with the onset of menstrual bleeding. Therefore, it is classified as a disease different from menstrual pain, which is caused by the peeling of the endometrium during menstruation.

Although the cause of premenstrual syndrome has not been clearly identified, lifestyle habits and social factors such as hormonal imbalance, genetic predisposition, ovulation and menstrual cycle, drug use, smoking, drinking, caffeine intake, eating habits, contraceptive use, emotional state, and marital status, as well as other factors such as age, body height, body weight, history of childbirth, menstrual history, stress, and the like, are known to be related to premenstrual syndrome. Recently, it has been reported that changes in female hormones and luteal hormone throughout the menstrual cycle may affect various brain neurotransmitters to thus induce the occurrence of premenstrual syndrome. In particular, it has been reported that hormonal problems such as imbalance of progesterone and estrogen and a decrease in serotonin level due to an increase in prolactin level play a very important role in the occurrence of premenstrual syndrome (Biqqs and Demuth, 2011; Imai et al., 2015; Schmidt et al., 2017).

Prolactin is a lactation-stimulating hormone secreted by eosinophilic cells of the anterior pituitary, and the level thereof is known to be increased by estrogen and decreased by dopamine secreted from the hypothalamus. In normal persons, the secretion of progesterone is higher than that of estrogen during the luteal phase, and thus the secretion of prolactin is stable, but in women suffering from premenstrual syndrome, the secretion of progesterone is lower than that of estrogen, thereby increasing the secretion of prolactin, and it has been reported that this increase in prolactin secretion induces premenstrual syndrome (Halbreich et al., 1976). Based thereon, Prefemin tablets (*Vitex agnus-castus* fruit extract), which exhibit prolactin secretion inhibitory efficacy, are sold as a representative premenstrual syndrome drug, and in clinical trials, symptoms such as irritability, depression, anger, headaches, breast pain, and the like, are known to be alleviated by about 50%.

However, there is no research on methods of preventing or treating premenstrual syndrome using *Chrysanthemum zawadskii*, which is used as a traditional medicine in Korea.

CITATION LIST

Patent Literature (Patent Document 1) Korean Patent Application Publication No. 10-2013-0076114
(Patent Document 2) Korean Patent Application Publication No. 10-2010-0044433
(Patent Document 3) Korean Patent Application Publication No. 10-2013-0092256

DISCLOSURE

Technical Problem

Accordingly, the present inventors recognized the importance of prevention and treatment of female premenstrual syndrome, and selected naturally occurring compounds showing efficacy of inhibiting prolactin secretion in pituitary cells and efficacy of proliferation of pituitary cells using various natural materials. As a result, a *Chrysanthemum zawadskii* extract was found to strongly inhibit prolactin secretion in pituitary cells, and a mixture thereof with a malt extract or with a malt extract and an aloe extract had an enhanced prolactin secretion inhibitory effect compared to the *Chrysanthemum zawadskii* extract alone. Moreover, in a hyperprolactinemia-induced animal model, the present composition effectively regulates the secretion of progesterone, so the commercialization potential thereof is very high as a composition for the prevention, amelioration, or treatment of premenstrual syndrome caused by imbalance of estrogen and progesterone.

Accordingly, an object of the present invention is to provide a pharmaceutical composition for preventing, ameliorating, or treating premenstrual syndrome containing a *Chrysanthemum zawadskii* extract, a mixture of a *Chrysanthemum zawadskii* extract and a malt extract, or a mixture of a *Chrysanthemum zawadskii* extract, a malt extract, and an aloe extract.

Another object of the present invention is to provide a functional health food composition for preventing and ameliorating premenstrual syndrome symptoms containing a *Chrysanthemum zawadskii* extract, a mixture of a *Chrysanthemum zawadskii* extract and a malt extract, or a mixture of a *Chrysanthemum zawadskii* extract, a malt extract, and an aloe extract.

The objects of the present invention are not limited to the foregoing. The objects of the present invention will be able to be clearly understood through the following description and to be realized by the means described in the claims and combinations thereof.

Technical Solution

An aspect of the present invention provides a composition for ameliorating, preventing, or treating premenstrual syndrome containing a *Chrysanthemum zawadskii* extract as an active ingredient.

The composition according to an aspect of the present invention may further contain a malt extract.

The composition according to an aspect of the present invention may further contain an aloe extract, in addition to the malt extract.

In the composition according to an aspect of the present invention, the extract may be an extract using water, a $C_1$-$C_5$ alcohol, or a $C_1$-$C_5$ alcohol aqueous solution.

In the composition according to an aspect of the present invention, the amount of the *Chrysanthemum zawadskii* extract may be 0.001 to 90 wt % based on the total weight of the composition.

In the composition according to an aspect of the present invention, the malt extract may be contained in an amount of 50 to 150 parts by weight based on 100 parts by weight of the *Chrysanthemum zawadskii* extract.

In the composition according to an aspect of the present invention, the malt extract may be contained in an amount of 50 to 150 parts by weight based on 100 parts by weight of the *Chrysanthemum zawadskii* extract, and the aloe extract may be contained in an amount of 10 to 30 parts by weight based on 100 parts by weight of the *Chrysanthemum zawadskii* extract.

In the composition according to an aspect of the present invention, the *Chrysanthemum zawadskii* extract may be an extract using a 60% to 80% ethanol aqueous solution, the malt extract may be an extract using a 40% to 60% ethanol aqueous solution, and the aloe extract may be an extract using a 20% to 40% ethanol aqueous solution.

The composition according to an aspect of the present invention may inhibit secretion of prolactin or increase secretion of progesterone in women in a luteal phase before menstruation.

In the composition according to an aspect of the present invention, the premenstrual syndrome symptoms may include at least one selected from among minor psychological distress, bloating, weight gain, breast tenderness, muscle tension or aches, poor concentration, and changes in appetite, and the premenstrual syndrome symptoms may appear only in the luteal phase of a menstrual cycle.

The composition for preventing or treating premenstrual syndrome according to an aspect of the present invention may be a pharmaceutical composition.

The composition for ameliorating premenstrual syndrome according to an aspect of the present invention may be a functional health food composition.

Advantageous Effects

According to the present invention, a *Chrysanthemum zawadskii* extract contained as an active ingredient in the composition of the present invention effectively inhibits prolactin secretion in pituitary cells and increases the secretion of progesterone in the luteal phase. Moreover, the composition containing the *Chrysanthemum zawadskii* extract serving as an active ingredient in combination with a malt extract or with both a malt extract and an aloe extract is very effective at inhibiting prolactin secretion in pituitary cells and controlling the secretion of progesterone. Therefore, the *Chrysanthemum zawadskii* extract, the mixture of the *Chrysanthemum zawadskii* extract and the malt extract, or the mixture of the *Chrysanthemum zawadskii* extract, the malt extract, and the aloe extract is capable of ameliorating, preventing, or treating a disease requiring inhibition of prolactin secretion and increased secretion of progesterone, namely premenstrual syndrome.

The effects of the present invention are not limited to the foregoing. The effects of the present invention should be understood to include all effects that may be reasonably anticipated from the following description.

BEST MODE

Figure 1:
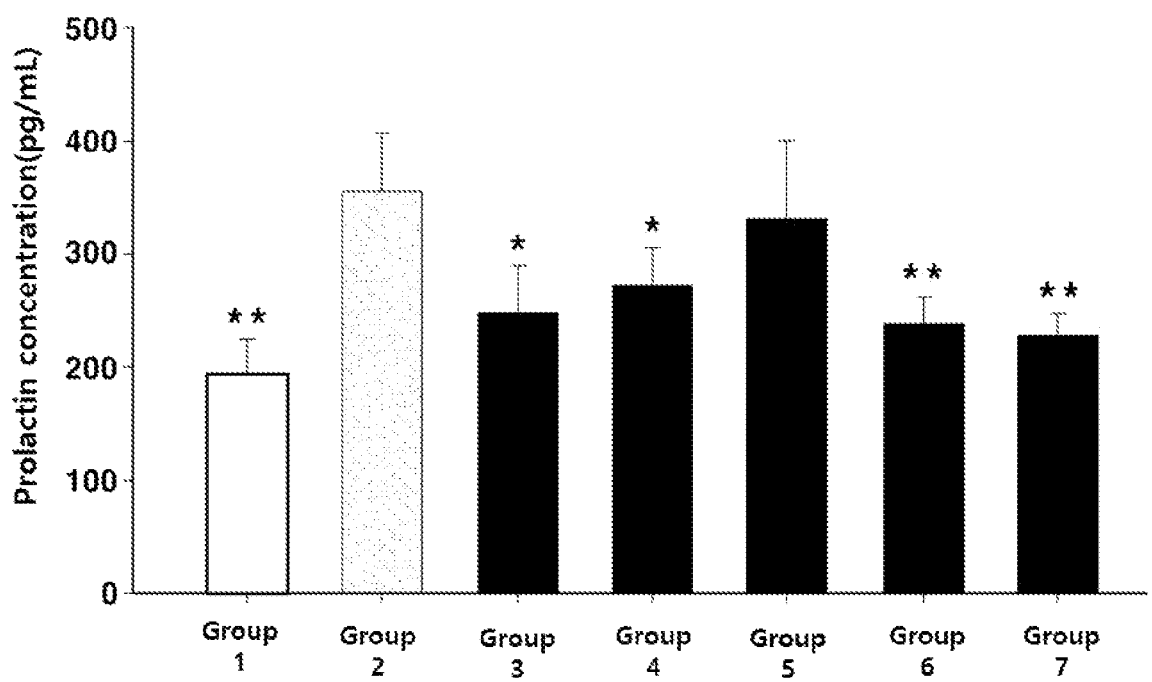
FIG. 1 shows the efficacy of inhibition of prolactin secretion by administration of the composition of the present invention to an animal model of hyperprolactinemia (Experimental Example 4)

Unless otherwise specified, all numbers, values, and/or representations that express the amounts of ingredients, reaction conditions, and compositions used herein are to be taken as approximations including various uncertainties affecting measurement that inherently occur in obtaining these values, among others, and thus should be understood to be modified by the term "about" in all cases. Furthermore, when a numerical range is disclosed in this specification, the range is continuous, and includes all values from the minimum value of said range to the maximum value thereof, unless otherwise indicated. Moreover, when such a range pertains to integer values, all integers including the minimum value to the maximum value are included, unless otherwise indicated.

In the present specification, when a range is described for a variable, it will be understood that the variable includes all values including the end points described within the stated range. For example, the range of "5 to 10" will be understood to include any subranges, such as 6 to 10, 7 to 10, 6 to 9, 7 to 9, and the like, as well as individual values of 5, 6, 7, 8, 9 and 10, and will also be understood to include any value between valid integers within the stated range, such as 5.5, 6.5, 7.5, 5.5 to 8.5, 6.5 to 9, and the like. Also, for example, the range of "10% to 30%" will be understood to include subranges, such as 10% to 15%, 12% to 18%, 20% to 30%, etc., as well as all integers including values of 10%, 11%, 12%, 13% and the like up to 30%, and will also be understood to include any value between valid integers within the stated range, such as 10.5%, 15.5%, 25.5%, and the like.

Hereinafter, a detailed description will be given of the present invention.

The present invention pertains to a composition for preventing, ameliorating, or treating premenstrual syndrome containing (a) a *Chrysanthemum zawadskii* extract, (b) a mixture of a *Chrysanthemum zawadskii* extract and a malt extract, or (c) a mixture of a *Chrysanthemum zawadskii* extract, a malt extract, and an aloe extract. Specifically, the present composition may be useful for preventing, ameliorating, or treating female premenstrual syndrome by effectively inhibiting prolactin secretion in pituitary cells, which is a phenomenon that occurs in premenstrual syndrome, thus increasing the decrease in progesterone secretion in the luteal phase of women.

*Chrysanthemum zawadskii* (*Chrysanthemum zawadskii* Herbich var. *latilobum* (Maxim.) Kitamura) is a perennial herb belonging to the Compositae family, and the whole plant is used as herbal medicine and has been used in oriental medicine and folklore for treatment of pneumonia, bronchitis, bladder disease, uterus coldness, menstrual irregularity, gastrointestinal disease, high blood pressure, and the like. The main components of *Chrysanthemum zawadskii* are reported to be flavonoid compounds such as linarin, coumarin compounds such as hydroxycoumarin, scopoletin and esculetin, polyacetylene compounds, sesquiterpene lactone compounds such as angeloylcumambrin B and cumambrin A, and essential oil components such as chamazulene. Here, the *Chrysanthemum zawadskii* extract and linarin have anti-inflammatory activity, antipyretic activity, and hepatoprotective activity, and sesquiterpene lactone has anti-tumor activity, cancer cytotoxicity, allelopathy, antibacterial action, and insecticidal action, as well as various pharmacological activities such as protective action of gastrointestinal cells, analgesic action, antioxidant action, and the like. *Chrysanthemum zawadskii* is an herbal material used in oriental medicine for the treatment of menstrual irregularity, but menstrual irregularity is a disease that generally shows no menstruation or irregular menstruation, and includes rare ovulation and anovulation. Therefore, menstruation irregularity is clearly distinguished from premenstrual syndrome, which shows breast tenderness and psychological symptoms in the luteal phase before menstruation, which must occur. In addition, none of the documents published to date have revealed that a *Chrysanthemum zawadskii* extract and main components thereof are effective at preventing, ameliorating, or treating female premenstrual syndrome due to inhibition of prolactin secretion.

Malt (*Hordei fructus germinatus*), which is contained in the mixture of the present invention, is a medicinal material made by lightly roasting the sprouts of barley, a member of the grass family, after drying the same. It is used in oriental medicine to treat digestive disorders caused by spleen-stomach weakness, and in particular, traditional use of malt has been reported when the secretion of milk is excessive. Wang et al. (2014) reported that a malt extract using water inhibits prolactin secretion by inducing activation of dopamine receptors, and Sommer et al. (2017) reported that hordenine, which is a component of malt, is an agonist of dopamine receptors. However, in the present invention, when the malt extract is used in a mixture with a *Chrysanthemum zawadskii* extract or an aloe extract, rather than alone, the secretion of prolactin is more effectively inhibited, so it is provided in the form of a mixture in the composition of the present invention.

Aloe is a perennial plant in the Liliaceae family, and contains aloin (barbaloin), isobarbaloin, β-barbaloin, and resin, and has been traditionally used for the treatment of skin disorders such as skin cancer, burns, eczema, psoriasis, and the like. It has been reported to have skin-moisturizing effects, erythema inhibitory effects, antioxidant effects, wound-healing effects, laxative effects, antibacterial effects, and anti-osteoporosis effects. In the present invention, an aloe extract was adopted as a material capable of alleviating side effects that may occur when inhibiting prolactin secretion by applying the effect of proliferation of pituitary cells. When mixed with either or both of *Chrysanthemum zawadskii* and malt, aloe inhibited the secretion of prolactin more effectively, and thus it is provided in the form of a mixture in the composition of the present invention. Moreover, none of the documents published to date has revealed that the aloe extract exhibits the effect of proliferation of pituitary cells and is effective for preventing, ameliorating, or treating female premenstrual syndrome due to inhibition of prolactin secretion.

The present invention provides a pharmaceutical composition for preventing and treating premenstrual syndrome containing a *Chrysanthemum zawadskii* extract, a mixture of a *Chrysanthemum zawadskii* extract and a malt extract, or a mixture of a *Chrysanthemum zawadskii* extract, a malt extract, and an aloe extract. The mixture may be an extract of a mixture of *Chrysanthemum zawadskii* and malt, an extract of a mixture of *Chrysanthemum zawadskii*, malt, and aloe, a mixture of a *Chrysanthemum zawadskii* extract and a malt extract, or a mixture of a *Chrysanthemum zawadskii* extract, a malt extract, and an aloe extract. The *Chrysanthemum zawadskii* extract and the malt extract may take the form of a liquid extract or a freeze-dried powder of the liquid extract, and the aloe extract may take the form of a liquid extract or a freeze-dried powder of the liquid extract, and may be a freeze-dried powder of aloe.

In addition, the present invention provides a functional health food composition for preventing and ameliorating premenstrual syndrome containing a *Chrysanthemum zawadskii* extract, a mixture of a *Chrysanthemum zawadskii* extract and a malt extract, or a mixture of a *Chrysanthemum zawadskii* extract, a malt extract, and an aloe extract. The mixture may be an extract of a mixture of *Chrysanthemum zawadskii* and malt, an extract of a mixture of *Chrysanthemum zawadskii*, malt, and aloe, a mixture of a *Chrysanthemum zawadskii* extract and a malt extract, or a mixture of a *Chrysanthemum zawadskii* extract, a malt extract, and an aloe extract. Moreover, the *Chrysanthemum zawadskii* extract, the malt extract, and the aloe extract may take the form of a liquid extract or a freeze-dried powder of the liquid extract.

Various aspects of the present invention are described below.

An aspect of the present invention provides a composition for ameliorating, preventing, or treating premenstrual syndrome containing a *Chrysanthemum zawadskii* extract as an active ingredient.

The composition according to an aspect of the present invention further contains a malt extract. In one embodiment, the active ingredient may be contained in an amount of 20 to 60 wt % based on the total weight of the composition, but the present invention is not limited thereto.

The composition according to an aspect of the present invention further contains an aloe extract, in addition to the malt extract. In one embodiment, the active ingredient of the aloe extract may be contained in an amount of 0 to 30 wt % based on the total weight of the composition, but the present invention is not limited thereto.

These compositions effectively inhibit prolactin secretion in pituitary cells, and increase the secretion of progesterone during the luteal phase. Moreover, the compositions are natural materials that have been conventionally ingested and taken, and may thus be safely used for preventing, ameliorating, or treating premenstrual syndrome.

The *Chrysanthemum zawadskii* extract may be obtained by extracting *Chrysanthemum zawadskii* through a typical extraction method, and may be an extract in a powder form, obtained by subjecting the extract to drying under reduced pressure and freeze-drying. The malt extract may be obtained by extracting malt through a typical extraction method, and may be an extract in a powder form, obtained by subjecting the extract to drying under reduced pressure and freeze-drying. Also, the aloe extract may be extracted through a typical extraction method, and may be an extract in a powder form, obtained by subjecting the extract to drying under reduced pressure and freeze-drying, and may be a freeze-dried powder obtained through freeze-drying immediately after peeling the skin of aloe.

The *Chrysanthemum zawadskii* extract and the malt extract in the mixture may be contained in respective amounts of 20 to 60 wt %, and the aloe extract may be contained in an amount of 0 to 30 wt %.

In the composition according to an aspect of the present invention, the extract is obtained using water, a $C_1$-$C_5$ alcohol, or a $C_1$-$C_5$ alcohol aqueous solution.

The composition for preventing, ameliorating, or treating premenstrual syndrome containing the components described above according to the present invention may be obtained in a liquid form by extracting *Chrysanthemum zawadskii*, malt, and aloe alone or in combination using an extraction solvent, such as water, alcohol, ethanol, or a mixture thereof according to a typical method, and the extraction process may be repeated as necessary, and an extract obtained by repeating the extraction process 2 to 5 times may be used. Moreover, a dry powdery extract obtained by freeze-drying the above extract may be prepared and used in the composition for preventing, ameliorating, or treating premenstrual syndrome.

The amount of alcohol in the extraction solvent is 0 to 95 wt %, preferably 30 to 70 wt %, and more preferably about 70 wt %, 50 wt %, and 30 wt % for *Chrysanthemum zawadskii*, malt, and aloe, respectively, in view of extraction efficiency. Any alcohol may be used, so long as it is typical in the art, and is preferably a $C_1$-$C_5$ alcohol. The alcohol may be at least one selected from methanol, ethanol, isopropanol, propanol, and butanol. More preferably, the alcohol is ethanol, grain alcohol (ethanol), or the like.

The extraction method is a method commonly known in the art, for example, a method using an extraction device such as supercritical extraction, subcritical extraction, high-temperature extraction, high-pressure extraction, or ultra-sonic extraction, or using an adsorption resin including XAD and HP-20.

In addition, an extract is obtained by subjecting the extract solution to concentration under reduced pressure using a vacuum rotary evaporator or the like. Moreover, the extract thus obtained may also be subjected to drying under reduced pressure, vacuum drying, boiling drying, spray drying, room-temperature drying, or freeze-drying, as necessary. In particular, when freeze-drying is performed, there is an advantage in that loss of volatile organic materials in the extract may be reduced.

The *Chrysanthemum zawadskii* extract obtained through the above method effectively inhibits prolactin secretion in pituitary cells, and increases the secretion of progesterone in the luteal phase. Also, the composition obtained by mixing the *Chrysanthemum zawadskii* extract and the malt extract or mixing the *Chrysanthemum zawadskii* extract, the malt extract, and the aloe extract, obtained through the above method, is more effective at inhibiting prolactin secretion in pituitary cells and controlling the secretion of progesterone.

In the composition according to an aspect of the present invention, the amount of the *Chrysanthemum zawadskii* extract is 0.001 to 90 wt % based on the total weight of the composition.

In the composition according to an aspect of the present invention, the malt extract is contained in an amount of 50 to 150 parts by weight based on 100 parts by weight of the *Chrysanthemum zawadskii* extract.

In the composition according to an aspect of the present invention, the malt extract is contained in an amount of 50 to 150 parts by weight based on 100 parts by weight of the *Chrysanthemum zawadskii* extract, and the aloe extract is contained in an amount of 10 to 30 parts by weight based on 100 parts by weight of the *Chrysanthemum zawadskii* extract.

When the composition including the *Chrysanthemum zawadskii* extract, the malt extract, and the aloe extract mixed at the above weight ratio is provided, the effect of preventing and treating premenstrual syndrome may be vastly superior compared to when the extracts are used alone.

In the composition according to an aspect of the present invention, the *Chrysanthemum zawadskii* extract is an extract using a 60% to 80% ethanol aqueous solution, the malt extract is an extract using a 40% to 60% ethanol aqueous solution, and the aloe extract is an extract using a 20% to 40% ethanol aqueous solution.

When the composition including the *Chrysanthemum zawadskii* extract, the malt extract, and the aloe extract using the solvents in the above concentration ranges is provided, the effect of preventing and treating premenstrual syndrome may be vastly superior compared to when the extracts are used alone.

The composition according to an aspect of the present invention is capable of inhibiting the secretion of prolactin or increasing the secretion of progesterone in women in the luteal phase before menstruation.

In the present invention, the premenstrual syndrome symptoms include at least one selected from among minor psychological distress, bloating, weight gain, breast tenderness, muscular tension or aches, poor concentration, and changes in appetite, the premenstrual syndrome symptoms appearing only in the luteal phase of the menstrual cycle.

The composition for preventing or treating premenstrual syndrome according to an aspect of the present invention may be a pharmaceutical composition.

When the pharmaceutical composition is used clinically, it is blended with a carrier that is commonly used in the pharmaceutical field to prepare typical formulations, for example, formulations for oral administration, such as tablets, capsules, powders, granules, pills, liquids, and suspensions; injection preparations in the form of solutions or suspensions for injection, or ready-to-use dry powder for injection, which may be prepared with distilled water for injection at the time of injection; or various preparations such as ointment. Pharmaceutical formulations prepared using typical carriers may be administered orally or parenterally, for example, intravenously, subcutaneously, intraperitoneally, or topically. Accordingly, the pharmaceutical composition of the present invention may further include suitable carriers, excipients, and diluents commonly used for the manufacture of pharmaceuticals.

The carriers, excipients, and diluents that may be contained in the pharmaceutical composition of the present invention include at least one selected from among lactose, dextrose, sucrose, sorbitol, mannitol, xylitol, erythritol, maltitol, starch, acacia gum, alginate, gelatin, calcium phosphate, calcium silicate, cellulose, methyl cellulose, hydroxymethyl cellulose, microcrystalline cellulose, silicified microcrystalline cellulose, povidone, crospovidone, croscarmellose sodium, polyvinylpyrrolidone, water, methylhydroxybenzoate, propylhydroxybenzoate, Noisirin, colloidal silicon dioxide, talc, magnesium stearate, colloidal magnesium stearate, and mineral oil.

Formulations are prepared using commonly used diluents or excipients such as fillers, extenders, binders, wetting agents, disintegrants, surfactants, and the like. Solid formulations for oral administration include tablets, pills, powders, granules, troches, lozenges, capsules, and the like, and these solid formulations are prepared by mixing the composition of the present invention with at least one excipient, for example, lactose, saccharose, sorbitol, mannitol, starch, amylopectin, cellulose, calcium carbonate, gelatin, etc. In addition to simple excipients, lubricants such as magnesium stearate and talc are also used. Liquid formulations for oral administration include suspensions, internal solutions, emulsions, elixirs, syrups, etc. In addition to water and liquid paraffin, which are commonly used simple diluents, various excipients such as wetting agents, sweeteners, fragrances, preservatives, etc. may be included. Formulations for parenteral administration include sterile aqueous solutions, non-aqueous solutions, suspensions, emulsions, freeze-dried preparations, and suppositories. Non-aqueous solvents and suspension agents include propylene glycol, polyethylene glycol, vegetable oils such as olive oil, and injectable esters such as ethyl oleate. As the base of the suppository, Witepsol, macrogol, Tween 61, cacao butter, laurinum, glycerol gelatin, and the like may be used. Parenteral administration may be commonly carried out as subcutaneous injection, intravenous injection, intramuscular injection, or intrathoracic injection.

The preferred dosage of the pharmaceutical composition of the present invention varies depending on the patient's age, body weight, and severity of disease, as well as the drug form and administration route and period, but may be appropriately selected by those skilled in the art. However, for a desirable effect, the pharmaceutical composition of the present invention may be administered at a daily dose of 0.01 mg/kg to 10 g/kg, and preferably 1 mg/kg to 1 g/kg. Administration may be carried out several times a day, preferably 1 to 6 times a day, at regular time intervals according to the judgment of a doctor or pharmacist.

The composition for ameliorating premenstrual syndrome according to an aspect of the present invention may be a functional health food composition.

The functional health food composition according to the present invention contains, as an active ingredient, a *Chrysanthemum zawadskii* extract, a mixture of a *Chrysanthemum zawadskii* extract and a malt extract, or a mixture of a *Chrysanthemum zawadskii* extract, a malt extract, and an aloe extract, and may be ingested for the purpose of alleviating premenstrual syndrome symptoms. The active ingredient may be ingested as food prepared in tablets, capsules, powders, granules, pills, liquids, suspensions, or the like, or may be added to general food and ingested. Since the functional health food uses food as a raw material, unlike general drugs, there is an advantage in that there are no side effects that may occur when taking the drug for a long time. The amount of the active ingredient may be appropriately determined depending on the purpose of use thereof (for prevention or amelioration). In general, the amount of the active ingredient in the functional health food composition may be 0.1 to 90 wt %. However, for long-term intake for health and hygiene or health control, the amount thereof may be equal to or less than the lower limit of the above range, and as long as there is no problem in terms of safety, the active ingredient may be used in an amount equal to or greater than the upper limit of the above range.

There is no particular limitation on the type of food. Examples of food to which the active ingredient may be added include drinks, meat, sausages, bread, biscuits, rice cakes, chocolate, candy, snacks, confectioneries, pizza, ramen, other noodles, gum, dairy products including ice cream, various soups, beverages, alcoholic beverages, vitamin complexes, milk products, and processed milk products, and includes all functional health foods in the ordinary sense. The appearance of the food is also not particularly limited, and may be any of a solid form, a semi-solid form, a gel form, a liquid form, a powder form, and the like.

A beverage may be prepared using the functional health food composition of the present invention. With regard to components included in the beverage, there is no particular limitation on the selection of components other than the active ingredient, and as in a typical beverage, various flavoring agents or natural carbohydrates may be contained as additional components. Examples of the natural carbohydrates mentioned above include typical sugars such as monosaccharides, for example glucose, fructose, and the like, disaccharides, for example maltose, sucrose, and the like, and polysaccharides, for example dextrin, cyclodextrin, and the like, and sugar alcohols such as xylitol, sorbitol, erythritol, and the like. As flavoring agents other than those described above, natural flavoring agents (thaumatin, *stevia* extract (e.g. rebaudioside A, glycyrrhizin, etc.)) and synthetic flavoring agents (saccharin, aspartame, etc.) may be advantageously used. The proportion of the natural carbohydrate is generally about 1 to 20 g, preferably about 5 to 12 g, based on 100 ml of the composition of the present invention.

Also, the functional health food composition of the present invention contains as additives, in addition to the active ingredient, various nutrients, vitamins, minerals (electrolytes), flavors such as synthetic flavors and natural flavors, coloring agents, and thickeners (cheese, chocolate, etc.), pectic acid and salts thereof, alginic acid and salts thereof, organic acids, protective colloidal thickeners, pH adjusters, stabilizers, preservatives, glycerin, alcohols, carbonation agents used in carbonated beverages, and the like. Moreover, natural fruit juice and pulp for the production of fruit juice beverages and vegetable beverages may be contained. These components may be used alone or in combination. Although the proportion of these additives is not so important, such additives are generally used in the range of 0.1 to 20 wt % in the functional health food composition of the present invention.

MODE FOR INVENTION

A better understanding of the present invention may be obtained through the following examples. These examples are merely set forth to illustrate the present invention, and are not to be construed as limiting the scope of the present invention.

EXAMPLES AND COMPARATIVE EXAMPLES

Preparation Example 1: Preparation of *Chrysanthemum zawadskii* Extract

*Chrysanthemum zawadskii* was purchased from Gyeongdong Market, Korea, and the whole plant was dried in the shade and pulverized, after which 1 kg of pulverized *Chrysanthemum zawadskii* was extracted using 70% ethanol at 80° C. for 5 hours, concentrated, and then freeze-dried, thus obtaining 117.4 g of a *Chrysanthemum zawadskii* extract (yield 11.7%).

Comparative Examples 1 to 4

As comparative examples, *Chrysanthemum zawadskii* extracts using hot water (Comparative Example 1), 30% ethanol (Comparative Example 2), 50% ethanol (Comparative Example 3), and 95% ethanol (Comparative Example 4) were used.

Preparation Example 2: Preparation of Malt Extract

Malt was purchased from Gyeongdong Market, Korea, dried in the shade, and pulverized, after which 1 kg of pulverized malt was extracted using 50% ethanol at 80° C. for 5 hours, concentrated, and then freeze-dried, thus obtaining 91.5 g of a malt extract (yield 9.1%).

Comparative Examples 5 to 8

As comparative examples, malt extracts using hot water (Comparative Example 5), 30% ethanol (Comparative Example 6), 70% ethanol (Comparative Example 7), and 95% ethanol (Comparative Example 8) were used.

Preparation Example 3: Preparation of Aloe Extract

Aloe was purchased from Samda Aloe Farm in Jeju, Korea, dried in the shade, and then finely cut, after which 1 kg of finely cut aloe was extracted using 30% ethanol at 80° C. for 5 hours, concentrated, and then freeze-dried, thus obtaining 11.0 g of an aloe extract (yield 1.1%).

Comparative Examples 9 to 12

As comparative examples, aloe extracts using hot water (Comparative Example 9), 50% ethanol (Comparative Example 10), 70% ethanol (Comparative Example 11), and 95% ethanol (Comparative Example 12) were used.

Preparation Example 4: Preparation of Mixture

The extracts obtained in Preparation Examples 1, 2, and 3 were mixed at the ratios shown in Table 1 below.

TABLE 1

|      | Chrysanthemum zawadskii extract using 70% ethanol | Malt extract using 50% ethanol | Aloe extract using 30% ethanol |
|------|----|----|----|
| 4-1  | 1  | 0  | 0  |
| 4-2  | 0  | 1  | 0  |
| 4-3  | 0  | 0  | 1  |
| 4-4  | 1  | 1  | 0  |
| 4-5  | 0  | 1  | 1  |
| 4-6  | 1  | 0  | 1  |
| 4-7  | 1  | 1  | 1  |
| 4-8  | 2  | 1  | 1  |
| 4-7  | 1  | 2  | 1  |
| 4-10 | 1  | 1  | 2  |
| 4-11 | 2  | 2  | 1  |
| 4-12 | 2  | 2  | 0.5 |
| 4-13 | 1  | 2  | 2  |
| 4-14 | 2  | 1  | 2  |
| 4-15 | 3  | 1  | 1  |
| 4-16 | 3  | 2  | 1  |
| 4-17 | 2  | 3  | 1  |
| 4-18 | 1  | 3  | 1  |

EXPERIMENTAL EXAMPLES

Experimental Example 1: Measurement of Pituitary Cell Proliferation Effect

In order to verify the pituitary cell protection effect of the aloe extract obtained in each of Preparation Example 3 and Comparative Examples corresponding thereto, the effect of proliferation of pituitary cells was measured.

Rat pituitary cells GH3 were purchased from ATCC (American Type Culture Collection), and DMEM culture medium, trypsin, and FBS (fetal bovine serum) were purchased from Gibco (Gibco™, Invitrogen Corporation).

GH3 pituitary cells were cultured in DMEM containing 10% serum and antibiotics using an incubator maintained at 37° C. with the supply of 5 vol % of carbon dioxide. GH3 cells were dispensed at a concentration of $5 \times 10^3$ cells/well in a 96-well plate and cultured for 24 hours. In order to measure the pituitary cell proliferation effect of the aloe extract, the medium was replaced with DMEM containing 10% charcoaled FBS, followed by treatment with the aloe extract at 25, 50, and 100 μg/mL. After 48 hours, the growth rate of GH3 cells was measured with absorbance at 550 nm using an MTT reagent, and the absorbance of each test solution was measured in comparison with a control to indicate the cell proliferation rate (%).

The GH3 pituitary cell proliferation rate of the aloe extract is shown in Table 2 below.

TABLE 2

|  | Pituitary cell proliferation rate compared to control (%) | | |
|---|---|---|---|
| Sample | 25 μg/mL | 50 μg/mL | 100 μg/mL |
| Aloe extract using hot water (Comparative Example 9) | 104.1 ± 1.31 | 116.1 ± 2.02 | 124.2 ± 2.88 |
| Aloe extract using 30% ethanol (Preparation Example 3) | 106.8 ± 1.18 | 112.2 ± 2.90 | 136.0 ± 2.46 |
| Aloe extract using 50% ethanol (Comparative Example 10) | 98.3 ± 1.03 | 99.8 ± 3.28 | 132.5 ± 2.97 |
| Aloe extract using 70% ethanol (Comparative Example 11) | 101.4 ± 1. 64 | 105.6 ± 2.15 | 122.5 ± 3.54 |
| Aloe extract using 95% ethanol (Comparative Example 12) | 96.4 ± 1.55 | 108.2 ± 2.56 | 116.4 ± 4.08 |
| Control | | 100.0 ± 3.69 | |

As is apparent from Table 2, the aloe extract using 30% ethanol exhibited the best pituitary cell proliferation efficacy, and exhibited a proliferation rate of about 136% compared to the control.

Experimental Example 2: Measurement of Prolactin Secretion Inhibitory Efficacy

The prolactin secretion inhibitory efficacy of each of the *Chrysanthemum zawadskii* extract and the malt extract obtained in Preparation Examples 1 and 2 and Comparative Examples corresponding thereto (Comparative Examples 1 to 8) and mixtures thereof was measured using pituitary cells.

The test cells, medium, medium composition, and experimental conditions were the same as in Experimental Example 1, and a prolactin ELISA kit for measurement was purchased from Mol-Innovations and used.

GH3 pituitary cells were dispensed at a concentration of $4 \times 10^4$ cells/well in a 24-well plate and cultured for 24 hours. For evaluation of prolactin secretion inhibitory efficacy, the cells were treated with each of the *Chrysanthemum zawadskii* extract and the malt extract at 25, 50, and 100 μg/mL and cultured for 48 hours, after which the amount of prolactin secretion was measured by being substituted into a standard curve using a rat prolactin ELISA kit.

The prolactin secretion inhibitory efficacy of the *Chrysanthemum zawadskii* extract and the malt extract is shown in Table 3 below.

TABLE 3

| Sample | Prolactin secretion (ng/mL) | | |
|---|---|---|---|
| | 25 µg/mL | 50 µg/mL | 100 µg/mL |
| *Chrysanthemum zawadskii* extract using hot water (Comparative Example 1) | 1.81 ± 0.231 | 1.31 ± 0.188 | 1.19 ± 0.121 |
| *Chrysanthemum zawadskii* extract using 30% ethanol (Comparative Example 2) | 1.74 ± 0.165 | 1.29 ± 0.132 | 1.00 ± 0.067 |
| *Chrysanthemum zawadskii* extract using 50% ethanol (Comparative Example 3) | 1.90 ± 0.206 | 1.30 ± 0.101 | 1.00 ± 0.085 |
| *Chrysanthemum zawadskii* extract using 70% ethanol (Preparation Example 1) | 1.72 ± 0.131 | 1.44 ± 0.213 | 0.43 ± 0.065 |
| *Chrysanthemum zawadskii* extract using 95% ethanol (Comparative Example 4) | 1.63 ± 0.184 | 1.32 ± 0.152 | 0.61 ± 0.119 |
| Malt extract using hot water (Comparative Example 5) | 1.51 ± 0.132 | 1.18 ± 0.129 | 0.85 ± 0.063 |
| Malt extract using 30% ethanol (Comparative Example 6) | 1.39 ± 0.079 | 1.08 ± 0.111 | 0.83 ± 0.036 |
| Malt extract using 50% ethanol (Preparation Example 2) | 1.10 ± 0.022 | 0.91 ± 0.158 | 0.53 ± 0.036 |
| Malt extract using 70% ethanol (Comparative Example 7) | 0.98 ± 0.268 | 0.96 ± 0.243 | 0.53 ± 0.019 |
| Malt extract using 95% ethanol (Comparative Example 8) | 1.08 ± 0.231 | 0.89 ± 0.152 | 0.61 ± 0.094 |
| Control | | 1.61 ± 0.016 | |

As is apparent from Table 3, the *Chrysanthemum zawadskii* extract using 70% ethanol exhibited the best prolactin secretion inhibitory efficacy and thus an inhibitory rate of about 73.3% compared to the control, and the malt extracts using 50% and 70% ethanol showed similar efficacy when treated at a concentration of 100 µg/mL, but the malt extract using 50% ethanol showed better efficacy when treated at a concentration of 50 µg/mL. In the present invention, the *Chrysanthemum zawadskii* extract using 70% ethanol and the malt extract using 50% ethanol were used as constituents of the mixture.

Experimental Example 3

In order to establish the optimal mixing ratio of the extract mixture of the present invention, the mixing ratio of Preparation Example 4 of Table 1 was applied in the same manner as in Experimental Example 2 to determine the prolactin secretion inhibitory effect at a single concentration of 100 µg/mL, and the results thereof are shown in Table 4 below.

TABLE 4

| | Preparation Example 1 | Preparation Example 2 | Preparation Example 3 | Prolactin secretion (ng/mL) |
|---|---|---|---|---|
| 4-1 | 1 | 0 | 0 | 0.389 |
| 4-2 | 0 | 1 | 0 | 0.409 |
| 4-3 | 0 | 0 | 1 | 1.698 |
| 4-4 | 1 | 1 | 0 | 0.371 |
| 4-5 | 0 | 1 | 1 | 0.852 |
| 4-6 | 1 | 0 | 1 | 0.860 |
| 4-7 | 1 | 1 | 1 | 0.489 |
| 4-8 | 2 | 1 | 1 | 0.625 |
| 4-7 | 1 | 2 | 1 | 0.623 |
| 4-10 | 1 | 1 | 2 | 0.701 |
| 4-11 | 2 | 2 | 1 | 0.367 |
| 4-12 | 2 | 2 | 0.5 | 0.344 |
| 4-13 | 1 | 2 | 2 | 0.947 |
| 4-14 | 2 | 1 | 2 | 0.773 |
| 4-15 | 3 | 1 | 1 | 0.646 |
| 4-16 | 3 | 2 | 1 | 0.660 |
| 4-17 | 2 | 3 | 1 | 0.751 |
| 4-18 | 1 | 3 | 1 | 0.684 |
| 19 | | Control | | 1.641 |

As is apparent from Table 4, the *Chrysanthemum zawadskii* extract using 70% ethanol obtained in Preparation Example 1 and the malt extract using 50% ethanol obtained in Preparation Example 2 showed very good prolactin secretion inhibitory efficacy, but the aloe extract using 30% ethanol obtained in Preparation Example 3 did not exhibit efficacy. In addition, the mixture of Preparation Examples 1 and 2 exhibited prolactin secretion inhibitory efficacy better than that of the single extract of each of Preparation Examples 1 and 2, and the mixture of Preparation Examples 1, 2, and 3 at a ratio of 2:2:0.5 exhibited the best prolactin secretion inhibitory efficacy. Accordingly, the present invention makes it possible to provide a composition for preventing, ameliorating, or treating premenstrual syndrome having efficacy of inhibiting prolactin secretion in pituitary cells, including (a) a *Chrysanthemum zawadskii* extract, (b) a mixture of a *Chrysanthemum zawadskii* extract and a malt extract, or (c) a mixture of a *Chrysanthemum zawadskii* extract, a malt extract, and an aloe extract.

Experimental Example 4. Evaluation of Efficacy of Premenstrual Syndrome Relief in Hyperprolactinemia-Induced Animal Model Metoclopramide is used as an antiemetic drug, and increases the secretion of prolactin by inhibiting dopamine secretion, and accordingly, it is known as a drug that inhibits the secretion of progesterone, luteinizing hormone, and follicle-stimulating hormone (Wang et al., 2014). Therefore, in the present invention, 50 mg/kg of metoclopramide was administered to the abdominal cavity of female rats for 5 days, after which hyperprolactinemia was induced to establish an animal model of premenstrual syndrome caused by hormone secretion disorder.

Rats (females) were obtained from Raonbio, and were acclimatized for 1 week while general solid feed and water were freely supplied thereto. The environmental conditions of the animal room were set to a temperature of 23±3° C., a relative humidity of 50±10%, a lighting time of 12 hours (8 am to 8 pm), a ventilation frequency of 10 to 20 times/hour, and an illumination intensity of 150 to 300 Lux. During the experiment, the temperature and humidity of the animal room were automatically controlled using a thermo-hygrostat.

Experimental animal groups were divided into 1) a normal group, 2) a hyperprolactinemia-induced control group, 3) a treatment group administered with Preparation Example 1, 4) a treatment group administered with Preparation Example 2, 5) a treatment group administered with Preparation Example 3, 6) a treatment group administered with a mixture of Preparation Examples 1 and 2 at 1:1, and 7) a treatment group administered with a mixture of Preparation Examples 1, 2, and 3 at 2:2:0.5 (Preparation Example 4-12), in which groups 1 and 2 were administered with saline, and treatment groups 3-7 were orally administered with a test material at a concentration of 100 mg/kg for 30 days. After termination of the experiment, blood was collected, serum was isolated therefrom, and the amounts of secreted prolactin and progesterone in the serum were measured using an ELISA kit. The results thereof are depicted in FIGS. 1 and 2.

As shown in FIG. 1, prolactin levels in the serum were increased by metoclopramide, and all groups except for that of the aloe extract using 30% ethanol of Preparation Example 3 showed prolactin secretion inhibitory effects. In addition, the *Chrysanthemum zawadskii* extract using 70% ethanol of Preparation Example 1 exhibited a prolactin secretion inhibitory effect superior to that of the malt extract using 50% ethanol of Preparation Example 2, and the mixture of Preparation Examples 1 and 2 and the mixture of Preparation Examples 1, 2 and 3 gradually decreased the secretion of prolactin.

Figure 2:
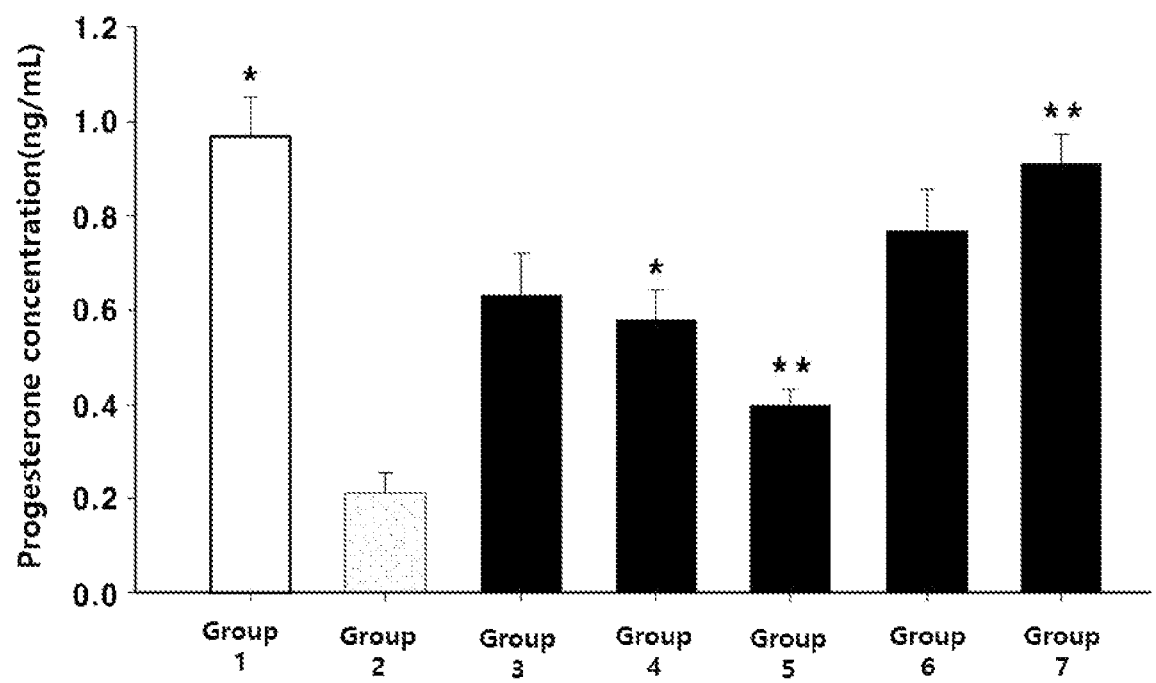
FIG. 2 shows the efficacy of increasing progesterone secretion by administration of the composition of the present invention to an animal model of hyperprolactinemia (Experimental Example 4).

As shown in FIG. 2, progesterone levels in the serum were decreased to about ⅕ by metoclopramide, and showed an increasing pattern in all treatment groups. Among these, the *Chrysanthemum zawadskii* extract using 70% ethanol of Preparation Example 1 showed a better effect of increasing progesterone secretion than the malt extract using 50% ethanol of Preparation Example 2, and the mixture of Preparation Examples 1 and 2 and the mixture of Preparation Examples 1, 2 and 3 exhibited a higher progesterone concentration than when the *Chrysanthemum zawadskii* extract, the malt extract, and the aloe extract were used alone.

In consideration thereof, (a) the *Chrysanthemum zawadskii* extract of the present invention, (b) the mixture of the *Chrysanthemum zawadskii* extract and the malt extract, or (c) the mixture of the *Chrysanthemum zawadskii* extract, the malt extract, and the aloe extract is capable of increasing lowered progesterone secretion that appears in premenstrual syndrome by inhibiting prolactin secretion in pituitary cells, and is thus effective for the prevention, amelioration, or treatment of premenstrual syndrome.

Although specific embodiments of the present disclosure have been described with reference to the accompanying drawings, those skilled in the art will appreciate that the present disclosure may be embodied in other specific forms without changing the technical spirit or essential features thereof. Thus, the embodiments described above should be understood to be non-limiting and illustrative in every way.

The invention claimed is:

1. A method for ameliorating or treating premenstrual syndrome, comprising administering a composition, comprising: *Chrysanthemum zawadskii* extract, and a malt extract as an active ingredient,
   wherein the *Chrysanthemum zawadskii* extract is an extract using a 60% to 80% ethanol aqueous solution, and the malt extract is an extract using a 40% to 60% ethanol aqueous solution,
   wherein the composition inhibits secretion of prolactin or increases secretion of progesterone in women in a luteal phase before menstruation,
   wherein the premenstrual syndrome appears in a luteal phase of a menstrual cycle, wherein the malt extract is prepared by extracting a malt, which is pulverized, using the 40% to 60% ethanol aqueous solution, and
   wherein the malt is derived from dried sprouts of barley.

2. The method of claim 1, wherein the composition further comprises an aloe extract.

3. The method of claim 2, wherein the malt extract is contained in an amount of 50 to 150 parts by weight based on 100 parts by weight of the *Chrysanthemum zawadskii* extract, and the aloe extract is contained in an amount of 10 to 30 parts by weight based on 100 parts by weight of the *Chrysanthemum zawadskii* extract.

4. The method of claim 2, wherein the aloe extract is an extract using a 20% to 40% ethanol aqueous solution.

5. The method of claim 2, further comprising, administering the composition as a pharmaceutical composition.

6. The method of claim 2, further comprising, administering the composition as a functional health food composition.

7. The method of claim 1, wherein an amount of the *Chrysanthemum zawadskii* extract is 0.001 to 90 wt % based on a total weight of the composition.

8. The method of claim 1, wherein the malt extract is contained in an amount of 50 to 150 parts by weight based on 100 parts by weight of the *Chrysanthemum zawadskii* extract.

9. The method of claim 1, wherein symptoms of the premenstrual syndrome comprise at least one selected from among minor psychological distress, bloating, breast tenderness, muscle tension or aches, poor concentration, and changes in appetite.

10. The method of claim 1, further comprising, administering the composition as a pharmaceutical composition.

11. The method of claim 1, further comprising, administering the composition as a functional health food composition.

* * * * *